United States Patent
Nitzsche et al.

[11] Patent Number: 5,891,170
[45] Date of Patent: Apr. 6, 1999

[54] METHOD AND APPARATUS FOR ADVANCED TACHYARRHYTHMIA DISCRIMINATION

[75] Inventors: Remi Nitzsche, Gambais; Jean-Luc Bonnet, Montrouge; Nicolas Iscolo, Saint Cyr l'Ecole; Marcel Limousin, Montrouge, all of France

[73] Assignee: ELA Medical, S.A., Montrouge, France

[21] Appl. No.: 877,039

[22] Filed: Jun. 17, 1997

[30] Foreign Application Priority Data

Oct. 18, 1996 [FR] France .................................. 96 07533

[51] Int. Cl.$^6$ ...................................................... A61N 1/39
[52] U.S. Cl. .............................................. 607/4; 600/518
[58] Field of Search ...................... 607/14, 4, 5; 600/518, 600/519, 515–517

[56] References Cited

U.S. PATENT DOCUMENTS

| 4,860,749 | 8/1989 | Lehmann et al. ................. 128/419 |
| 4,880,005 | 11/1989 | Pless et al. ..................... 600/518 |
| 5,193,535 | 3/1993 | Bardy et al. ..................... 128/419 |
| 5,205,283 | 4/1993 | Olson ........................... 600/518 |
| 5,342,402 | 8/1994 | Olson et al. ..................... 600/518 |
| 5,383,910 | 1/1995 | Den Dulk ........................ 607/14 |
| 5,411,530 | 5/1995 | Akhatar ......................... 607/14 |
| 5,462,060 | 10/1995 | Jacobson et al. ................. 128/702 |
| 5,562,709 | 10/1996 | White ........................... 600/518 |
| 5,759,196 | 6/1998 | Hess et al. ...................... 607/14 |

FOREIGN PATENT DOCUMENTS

| 0 540 141 A1 | 5/1993 | European Pat. Off. ....... A61N 1/368 |
| 0 550 344 A1 | 7/1993 | European Pat. Off. ......... A61N 1/39 |
| 0 626 182 A | 11/1994 | European Pat. Off. ....... A61N 1/368 |
| 94/16768 | 8/1994 | WIPO ........................ A61N 1/365 |

*Primary Examiner*—William E. Kamm
*Assistant Examiner*—Kennedy J. Schaetzle
*Attorney, Agent, or Firm*—Orrick, Herrington & Sutcliffe LLP

[57] ABSTRACT

An active implantable medical device of the defibrillator/cardiovertor type with advanced tachycardia discrimination in which the device monitors the atrial and ventricular activity, suspects and confirms the presence of tachycardia episodes in the monitored activity, and operates a classification algorithm to discriminate between ventricular tachycardias and supra-ventricular tachycardias according to predetermined criteria and a given adjustment of these criteria, and to authorize the releasing of a shock therapy defibrillation, and/or cardioversion and/or anti-tachycardia ventricular stimulation in the presence ventricular tachycardias and to inhibit delivery of a shock therapy in the presence of a supra-ventricular tachycardias, or instead to release an atrial therapy. The advanced discrimination modifies the classification operation by being able to add temporarily one or more criterion and/or to modify temporarily the adjustment of an existing (predetermined) criterion in case of a suspected atrial fibrillation. Added criterion include particularly a supplementary research criterion of short and/or long RR intervals, which are significantly distanced from a zone of RR interval stability, which significantly distanced zones are, for example, separated from the RR interval stability zone by a predetermined width interval, which width interval is identical on both sides of the RR interval stability zone.

20 Claims, 3 Drawing Sheets

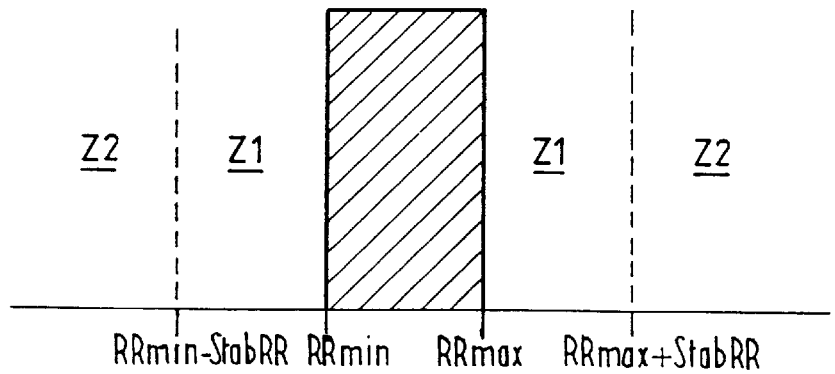
FIG_1
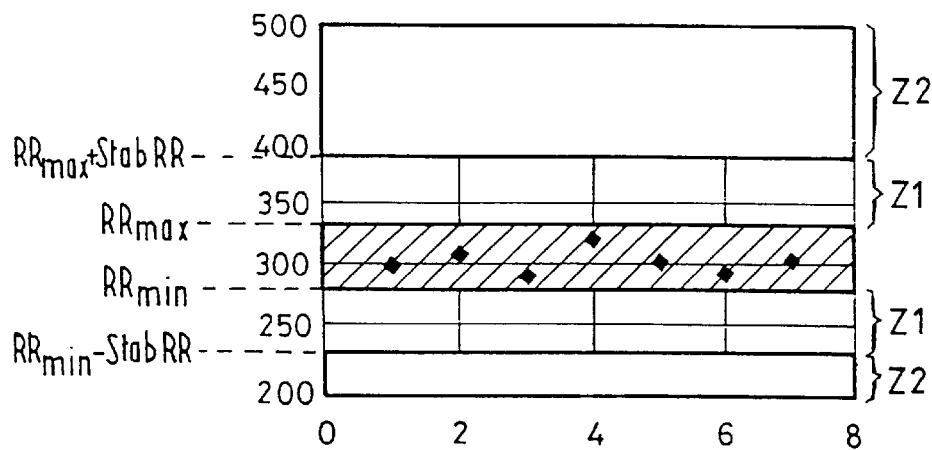
FIG_2
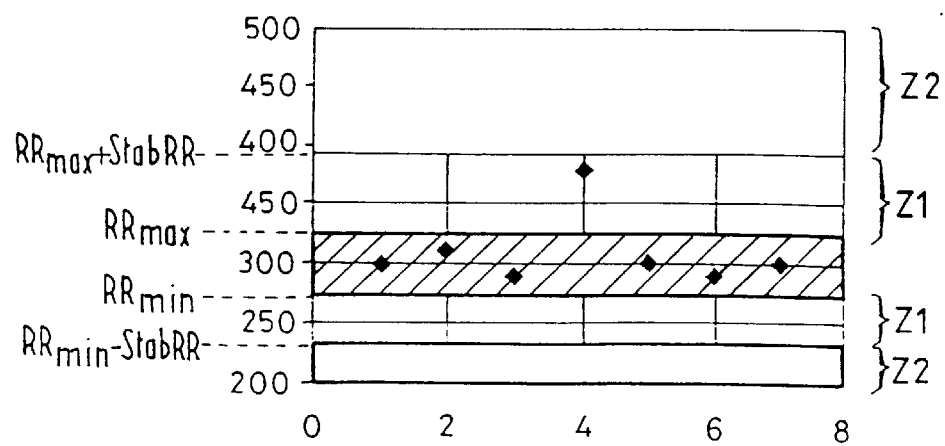
FIG_3

METHOD AND APPARATUS FOR ADVANCED TACHYARRHYTHMIA DISCRIMINATION

FIELD OF THE INVENTION

The present invention concerns active implantable medical devices, such as those defined by the Jun. 20, 1996 directive 90/385/EEC of the European Community Council), and more particularly the family of devices that deliver to the heart a mode of shock therapy including electrical impulses of high energy (that is to say energies substantially exceeding the energy typically provided for the simple stimulation) in order to stop to a tachyarrythmia. These modes of shock therapy include, among other things, a mode of programmed high frequency stimulation known as Anti Tachycardia Pacing ("ATP"). These devices are commonly called "implantable defibrillators" or "cardioversion devices" (and indeed the present invention is applicable to implantable defibrillators/cardioverters/pacemakers, as well as defibrillators/pacemakers).

BACKGROUND OF THE INVENTION

These devices comprise a pulse generator that is able to supervise (monitor) the cardiac activity of a patient and to generate shock pulses of high energy, which are applied to the heart when the heart presents a ventricular arrhythmia that is susceptible to be treated by a shock therapy. The pulse generator also is typically able to generate a stimulation pulse for stimulating a heart beat in the absence of a spontaneous contraction in one or both of the atrium and the ventricle. When the shock pulse of high energy is between approximately 0.1 and 10 J, one designates this shock therapy by the name of "cardioversion", and the electrical shock is called a "cardioversion shock." When the energy is greater than approximately 10 J, one designates this shock therapy "defibrillation" and the electrical shock is called a "defibrillation shock".

The high energy shock is to be delivered when one detects a ventricular tachycardia (VT), but only when it concerns a real VT, and not a supra-ventricular tachycardia (SVT). Indeed, in the case of an SVT, the tachycardia is of atrial origin and the shock that would be delivered to the ventricle would be without effect because the defibrillation electrode, or if needed the stimulation electrode, are not placed in the region of the atrium.

A tachyarrhythmia (also called a tachycardia) corresponds to an abnormal rapid cardiac rhythm and covers ventricular fibrillation (VF), ventricular tachycardia (VT), sinus tachycardia (ST) and supra-ventricular tachycardia (SVT). The supra-ventricular tachycardia (SVT) includes atrial tachycardia, atrial flutter, and atrial fibrillation. The diagnosis of a tachycardia is operated, in a manner that is known (see particularly, for example, EP-A-0 626 182 in the name of ELA Medical and its corresponding U.S. Pat. No. 5,462, 060, which is incorporated herein by reference), from criteria such as the ventricular frequency, the ventricular stability interval (RR interval), the analysis of the atrial-ventricular association, and the mode of starting of the tachycardia (that is, the presence of acceleration and the chamber of origin (ventricular or atrial)).

The diagnosis algorithm that provides for the detection of tachycardias and their classification (that is to say a discrimination between SVT and VT) is conceived in a manner to obtain a maximal sensitivity - to detect all ventricular tachycardias, thus avoiding the false negative diagnosis - while preserving the specificity of the discrimination - that is to say by accurately discriminating between SVT and VT, thus avoiding the false positive diagnosis. A false positive is an indication of a VT when it actually is an SVT. Further, this diagnosis algorithm allows to detect atrial fibrillations (AF), that is to say abnormally high frequencies of the atrial rhythm, and allows to distinguish an isolated AF (one that should not result in the delivery of a ventricular shock therapy) from a VT (one that should result in a rapid delivery of a ventricular shock therapy).

One observes, however, in some cases, a failure of the classification algorithm, particularly in the presence of an installed and conducted AF presenting regular RR intervals during a sufficiently long duration, which result in a false diagnosis of VT (i.e., a regular rhythm which is dissociated between the atria and ventricle). If one decreases the sensitivity of the classification algorithm to avoid such false diagnosis, one risks, on the one hand, to end the diagnosis algorithm without a detection of VT, and on the other hand, a lengthening of the analysis duration of the diagnosis algorithm.

The disadvantages are, in the first case, the risk of not detecting a real VT, and, in the second case, a lengthening of the period between the detection of the VT and the application of the appropriate shock therapy. The lengthening of the period is adverse to the well-being of the patient.

OBJECTS AND SUMMARY OF THE INVENTION

It is, therefore, an object of the invention is to overcome the foregoing difficulties, by proposing to improve existing devices so as to minimize, if not, eliminate, all risk of false diagnosis of VT in the presence of an installed and conducted AF, to increase the specificity of the analysis of tachycardias without compromising the sensitivity of the tachycardia, detection algorithm when started on a sinus rhythm.

One aspect of the invention is thus directed towards a medical device, such as a defibrillator or cardiovertor, of the type which comprises: means for delivering a shock therapy, preferably a shock therapy for defibrillation and/or cardioversion and/or ventricular anti-tachycardia pacing (ATP) stimulation; means for monitoring (detecting) atrial and ventricular activity; means for suspecting and confirming the presence of tachycardia episodes in the detected monitored activity; means for classification of the tachycardia, which is operative to discriminate between ventricular tachycardias and supra-ventricular tachycardias according to a predetermined criteria and a given adjustment of these criteria; and means to authorize delivery of a shock therapy in the presence of a ventricular tachycardia (i.e., a delivery the defibrillation, cardiovision or ATP shock, as may be appropriate under the circumstances), and to inhibit delivery of shock therapy in the presence of a supra-ventricular tachycardia. In a preferred embodiment, the classification means also is operative to release an atrial chamber therapy in the presence of a supra-ventricular tachycardia.

According to the invention, the aforementioned medical device comprises, in addition, an automatic means that operates to add temporarily one or more criterion and/or to modify temporarily the adjustment of an existing criterion in the case of suspected atrial fibrillation, thereby modifying the YE classification analysis.

The added criterion preferably comprises a supplementary research criterion of RR intervals having an RR interval range that is significantly different from the interval range for a stable RR interval (also referred to as an RR interval stability zone). More specifically, the research criterion may be a short RR interval range in which the RR intervals are shorter than those in the RR interval stability zone, a long RR interval range in which the RR intervals are longer than those in the RR interval stability range, or both. More preferably, the research criterion is both long and short RR intervals that are respectively separated from the limits of the RR interval stability zone by a predetermined width interval. The predetermined width interval is a time interval corresponding to a range of RR intervals, and the predetermined width interval is more preferably identical on both the long and the short RR interval sides of the stability zone.

The added criterion also can comprise a supplementary counting and comparison criterion of the number of atrial events, as compared to the number of ventricular events, during a given duration.

The modifiable adjustment can comprise, among other things: a majority parameter in which one evaluates, over a given number of cycles, the presence of a percentage, greater than or equal to a given threshold, of RR intervals that are outside of a given stability zone; a duration parameter of the persistence of tachycardias; and a width parameter of the stability zone.

The criteria and/or parameters of the means of classification are preferably restored (that is, reset) when episodes of supra-ventricular tachycardia are no longer confirmed in the monitored activity.

One also can foresee an embodiment in which, if one or more criterion are temporarily adjusted and/or the parameters are temporarily modified a determined number of times in the course of a given period, the addition and/or modification is then applied in a permanent manner. That is to say, the criteria and parameters are "permanently" modified by the then applied changes, and remain subject to further temporary and/or permanent modification in subsequent analyses.

BRIEF DESCRIPTION OF THE DRAWINGS

Other characteristics and advantages of the present invention will appear to a person of ordinary skill in the art in view of following detailed description, made with reference to the drawings annexed, in which FIGS. 1–3 illustrate the supplementary research criterion of long or short RR intervals significantly distanced from an RR interval stability zone and in which FIG. 1 is an RR interval histogram and FIGS. 2 and 3 are analysis diagrams of RR intervals.

DETAILED DESCRIPTION OF THE INVENTION

Figure 4:
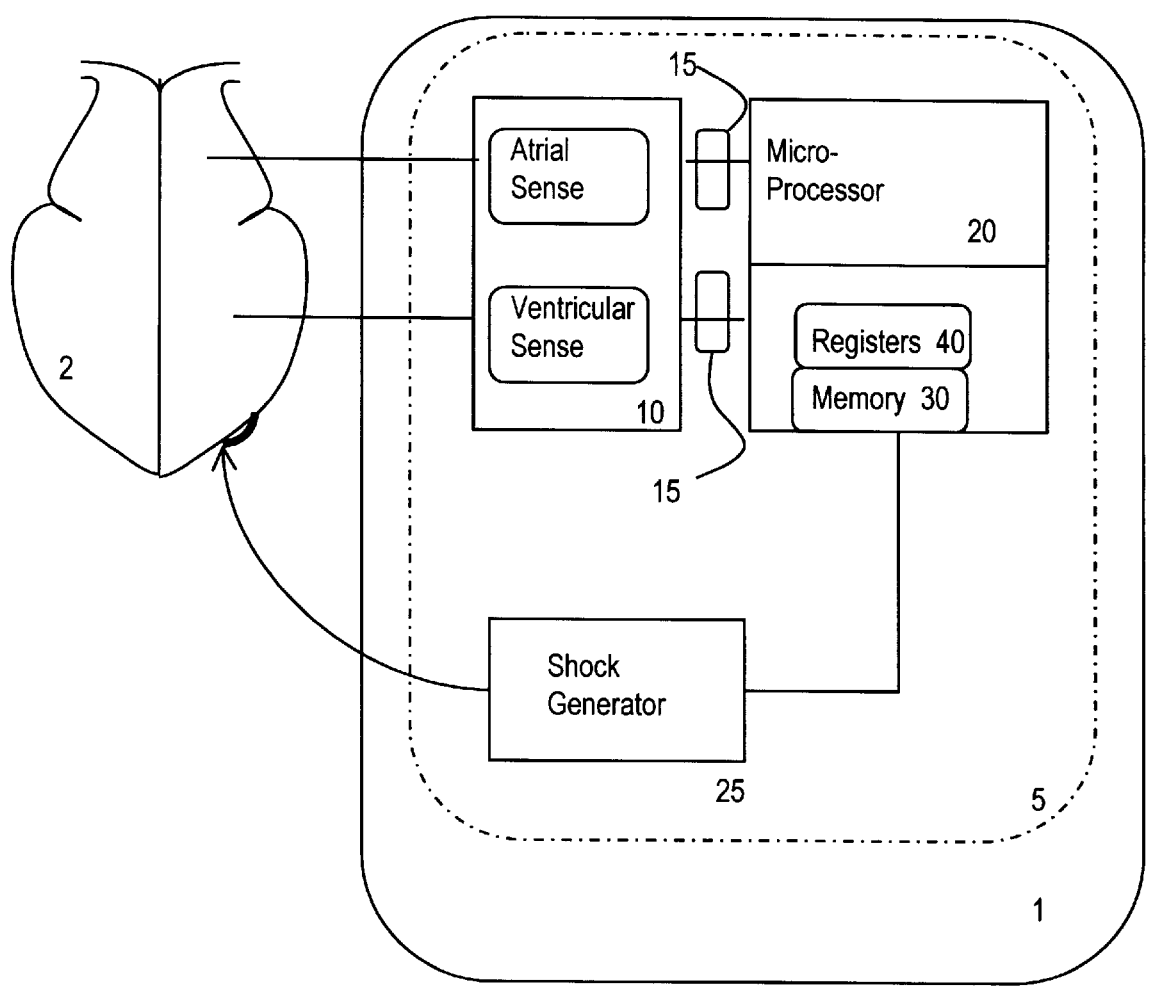
FIG. 4 is a block circuit schematic of one embodiment of an active implantable medical device according to an illustrative embodiment of the present invention.

The invention as discussed above concerns detecting an electrical activity in which there is a suspicion of the presence of a chronic or permanent AF having a regular rhythm (also known as an "installed AF" or a "conducted AF") and, if such is the case, to modifying temporarily the tachycardia classification parameters and/or the tachycardia classification criteria. This will increase the specificity of discrimination of the diagnosis algorithm, without decreasing in a significant manner its sensitivity to VT.

Among the tachycardia classification parameters that are currently used, and with which the programming can be modified, one finds essentially:

(1) A majority parameter (or "majority criterion"), according to which one undertakes a statistical analysis of a histogram of stored RR intervals over the course of a given number of cycles (a nominal parameter is, for example, 8 cycles) and one determines if one is in or is not in the presence of a percentage of RR intervals situated outside of the central peak of the RR interval stability zone that is greater than a given value (a nominal parameter is, for example, 75%); if such is the case, then one considers that the rhythm is regular and that there is no tachycardia;

(2) Persistence of the duration of the tachycardia episode (a nominal parameter is, for example, 8 cycles);

(3) the width of peak of the RR interval stability zone used for the detection of the regularity of the rhythm (a nominal parameter is, for example, 63 ms).

These parameters are, for example, implemented in an analysis algorithm for the tachycardia detection and classification of a defibrillator, such as the model Defender 9001 available from the assignee of this application, Ela Medical, Montrouge, France.

In accordance with an embodiment of the present invention, in the case of a detection of an installed AF, one modifies temporarily the criteria parameters (i.e., the nominal parameters or the parameters programmed by the physician), or one adds a criterion. For example, one lengthens the number of cycles used for the duration of detection of the majority parameter, for example, to 12 cycles, or perhaps to 16 cycles, or the persistence duration. To avoid delaying unnecessarily the time to deliver the therapy, it is preferable to increase only one of these two parameters, more preferably the persistence duration. One also can change the detection percentage of the majority parameter, for example, to 80%, or perhaps to 88%, preferably by, at the same time, increasing the number of cycles for the detection to decrease the effect of artifacts or the effect of a ventricular under-detection (that is, low amplitude R waves or slope), for example, by adjusting the criterion to 80% over 12 cycles or to 88% over 16 cycles.

In an alternative embodiment to the temporary modification of criteria parameters, one also can modify, in a temporary manner, the analysis algorithm by introducing one or more supplementary criterion, particularly a criterion to confirm that a VT is not superimposed on an AF. A first supplementary criterion, as illustrated on FIGS. 1 to 3, is to add to the criterion of RR interval stability a research criterion of long or short (or both long and short) RR interval cycles, which RR interval cycles occur in an interval range that is significantly distanced from the average RR interval distribution in the RR interval stability zone.

This average distribution or stability zone, illustrated with lines hatched on the Figures, is defined as a range centering on the position of the maximal amplitude peak in the RR Hi histogram (FIG. 1), this peak being limited on the short interval side by the RRMIN interval and on the long interval side by the RRMAX interval. The difference RRMAX–RRMIN is thus defined as the adjustment of the criterion of RR interval stability, as discussed below.

One defines then, on either side of the peak, two zones Z1 and Z2, as illustrated on FIG. 1, A first zone Z1 is situated near the peak or more preferably adjacent to the stability zone on either side, spreading, for example, over a range of from RRMIN–STABRR to RRMIN to the left on the short side of the peak, and RRMAX to RRMAX+STABRR to the right on the long side of the peak, and a second zone Z2 situated a significant distance from the peak, spreading, for example, from 0, or the value of the absolute ventricular refractory period, to RRMIN−STABRR to the left on the short side of the peak, and RRMAX+STABRR to 600 ms to the right on the long side of the peak. One then compares the number of RR interval falling in Zone Z2 (a significant distance from the peak, i.e. the RR interval stability zone) to the number of RR intervals falling in Zone Z1 (close to the peak). If, for example, as illustrated in FIG. 2, over the course of eight successive cycles, one finds no RR interval falling in Zone Z2, then one confirms the suspicion of a newly installed VT. On the other hand, if, as illustrated in FIG. 3, one finds at least one RR interval falling in Zone Z2, then one confirms the suspicion of an isolated AF and one continues the execution of the algorithm on this basis.

A second supplementary criterion that it is possible to foresee adding to the analysis algorithm is a count of the number of atrial events and ventricular events during a determined duration. If the number of atrial events is greater than the number of ventricular events, then one confirms the suspicion of an isolated AF. However, if the number of ventricular events becomes greater than or equal to the number of atrial events, then one confirms the suspicion of a newly installed VT (a case of "bi-tachycarda" AF+VT), and, in this case, the nominal detection algorithm is re-established with its nominal parameters that is the analysis algorithm is reset to its nominal parameters.

These two additional criteria can be used separately or jointly to continue to suspect an isolated AF.

In accordance with the invention, the modification of parameters of the algorithm and/or introduction of the additional criteria can be applied as long as the device is in suspicion of an installed SVT. This can be done either by the use of the fallback algorithm known "Repli" (such as is described in EP-A-0 488 840 and corresponding U.S. Pat. No. 5,226,415 commonly assigned to ELA Medical, the assignee hereof, which U.S. Patent is incorporated herein by reference in its entirety) or by any other means such as a metabolic sensor, hemodynamic sensor, cardiac output sensor, etc.

In the other cases, nominal parameters or parameters programmed by the physician and the nominal detection algorithm are applied. Furthermore, if the modification of parameters and/or the introduction of additional criterion is in use several times over a selected period, for example, 24 hours, then the device will apply these modifications in a "permanent" manner, that is, the parameters are reset to the "as-adjusted" values, a and the criterion being used will continue to be used. The number of repetitions which occur before the device does apply these modifications in a permanent manner is equal preferably to eight in a 24 hour period, although other periods and numbers of modifications could be used.

One also can apply the temporary modification when an installed SVT is confirmed by the tachycardia detection algorithm (in response to first a persistence of SVT), such that the nominal parameters or parameters programmed by the physician are applied again if the rhythm slows to below the programmed tachycardia frequency (typically 100 beats per minute).

Referring to FIG. 4, an active implantable medical device 1 of the defibrillator/cardiovertor type is shown with conventional electronic means 5 for performing the necessary functions for suspecting and confirming the presence of a tachycardia episode in the monitored activity and discriminating a suspected tachycardia episode as either a ventricular tachycardia and a supra-ventricular tachycardia according to adjustable predetermined criteria and for delivering shock therapy.

Electronic means 5 include, for example, digital microprocessor 20 controlled devices having sense amplifier 10, analog-to-digital conversion circuitry 15, memory 30 and registers 40 for data processing and manipulation and shock generator 25.

The present invention is preferably implemented under software control, and occurs in conjunction with acquisition of appropriate cardiac electric (i.e., atrial and ventricular activity) signals by conventional sense amplifiers, preferably after the acquired signals have been conditioned and converted to digital form in known manner. Accordingly, programmable parameters, such as predetermined criteria and threshold values, are useful in implementation of the method of the present invention.

Representative electronic circuits can be found in, for example, the model Defender 9001 defibrillator available from the assignee of this application, Ela Medical. The method may also be performed using discrete circuitry without departing from the scope of the invention.

Figure 5:
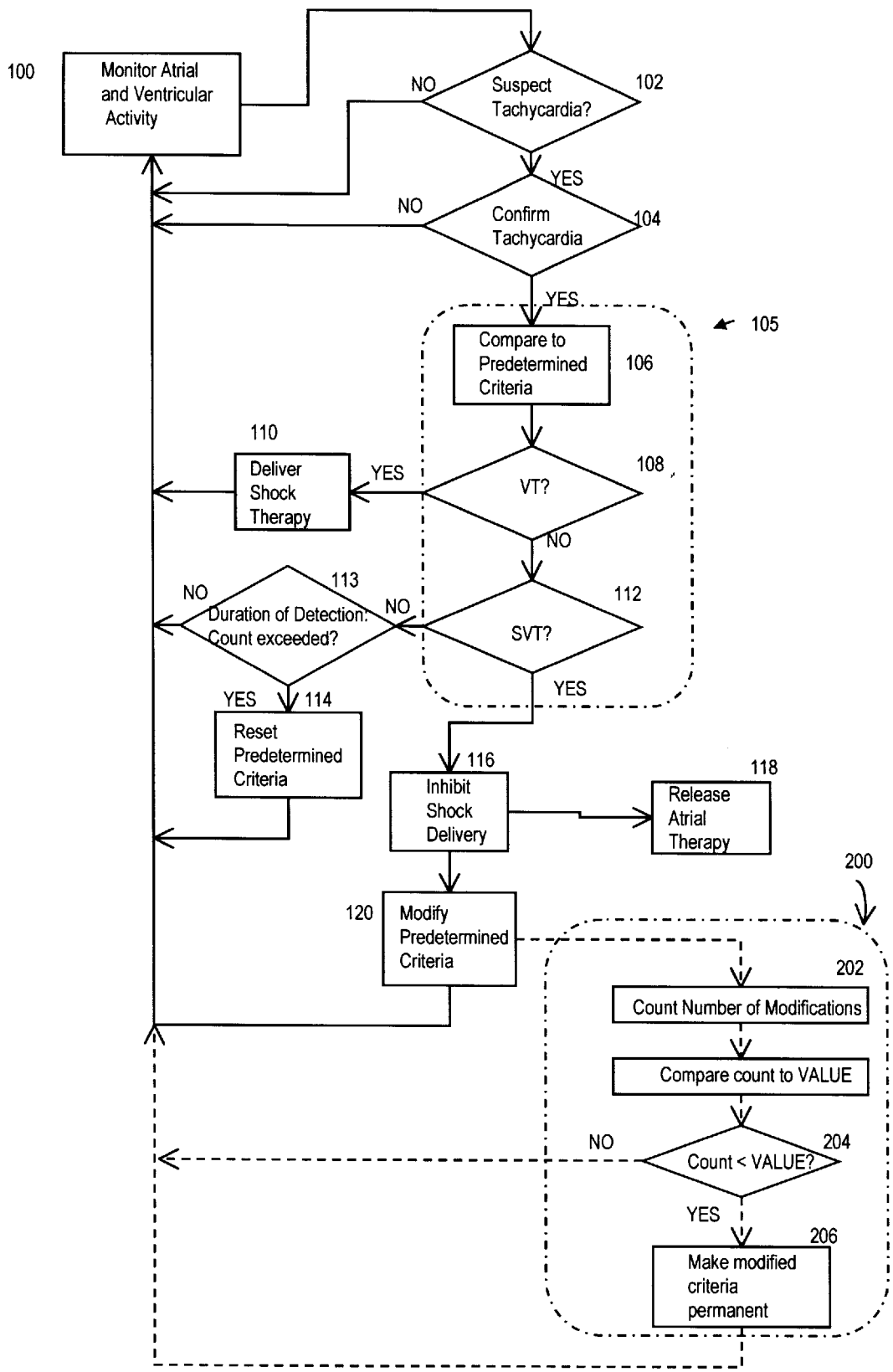
FIG. 5 illustrates a flow chart of an example sequence of operations implementable in the device of FIG. 4.

For a software controlled implantable medical device, one useful sequence of operations according to one embodiment of the method of the present invention are illustrated in FIG. 5 as follows.

Cardiac activity is monitored in terms of atrial and ventricular activity. (step 100) Based on the monitored signals, a determination is made whether Tachycardia suspected. (step 102). When suspected, the presence of Tachycardia is confirmed. (step 104). Classification of the confirmed Tachycardia and Shock Therapy Authorization occurs as illustrated in sequence box 105 where a comparison is made to a Predetermined Criteria. (step 106). Based on the comparison it is possible to classify the Tachycardia as either Ventricular Tachycardia ("VT") or SupraVentricular Tachycardia ("SVT"). If the confirmed Tachycardia is VT (step 108), shock therapy is authorized and delivered. (step 110). If the confirmed Tachycardia is not VT, a comparison determines whether the Tachycardia is SVT. (step 112). If not determined to be SVT, the duration of detection is verified to determine whether a predetermined count has been exceeded. (step 113). If the count is exceeded, the Predetermined Criteria is reset. (step 114). If SVT is determined, shock therapy is inhibited (step 116) and atrial therapy is released. (step 118). The predetermined criteria is updated and modified. (step 120 ). In sequence box 200, a determination is made as to the permanency of any such predetermined criteria adjustments, where the number of modifications to predetermined criteria is counted (step 202) and compared to a threshold value (step 204). If the threshold is exceeded, the criteria modification is deemed permanent (step 206).

This illustrative sequence will run in a continuous loop during expected operation.

One skilled in the art will appreciate that the present invention can be practiced by other than the described embodiments, which are provided for purposes of illustration and not of limitation.

We claim:

1. An active implantable medical device of the defibrillator/cardiovertor type, comprising:
   means for delivering a shock therapy;
   means for monitoring atrial and ventricular activity;
   means for suspecting and confirming the presence of a tachycardia episode in the monitored activity;
   means of classification, operable to discriminate a suspected tachycardia episode as between a ventricular tachycardia and a supra-ventricular tachycardia according to a predetermined criteria and a given adjustment of said predetermined criteria, and to authorize delivery of a shock therapy in the presence of a ventricular tachycardia and to inhibit delivery of a shock therapy in the presence of a supra-ventricular tachycardia and said classification means further comprising means for modifying said discrimination operation, in response to a supra-ventricular tachycardia, by one of adding temporarily at least one criterion and modifying temporarily the adjustment of a predetermined criterion.

2. The device of claim 1, wherein the added criterion further comprises a supplementary research criterion of at least one of a short RR interval range and a long RR interval range, said one RR interval range being significantly distanced from an RR interval stability zone.

3. The device of claim 2, wherein the RR interval stability zone further comprises a first limit and a second limit defining said RR interval stability zone, and the research criterion further comprises a long RR interval range and a short RR interval range respectively separated from the first and second limits by a predetermined width interval on each side of the RR interval stability zone.

4. The device of claim 1, in which the added criterion comprises a supplementary counting and comparison criterion corresponding to a number of atrial events relative to a number of ventricular events during a given duration.

5. The device of claim 1, in which the modifiable adjustment comprises a majority parameter and means for evaluating the majority parameter over a number of given cycles and determining the presence of a percentage, greater than or equal to a given threshold, of the RR intervals situated outside of a predetermined RR interval stability zone.

6. The device of claim 5, in which the modifiable adjustment comprises a duration parameter of tachycardia persistence.

7. The device of claim 5, in which the modifiable adjustment comprises a width parameter of an RR interval stability zone.

8. The device of claim 1, in which the predetermined criteria and/or parameters of the classification means are restored in response to an absence of a confirmed supra-ventricular tachycardia episode in the monitored activity.

9. The device of claim 1, further comprising means for determining if one or more criterion are temporarily adjusted and/or the temporarily modified adjustment is in use a determined number of times in the course of a predetermined period, and for applying the addition and/or modification in a permanent manner.

10. The device of claim 1 further comprising means for releasing an atrial therapy in response to a detected supra-ventricular tachycardia.

11. A method for discriminating tachycardia episodes in an active implantable medical device of the defibrillator/cardiovertor type for delivering a shock therapy, comprising:

monitoring atrial and ventricular activity;

identifying a tachycardia episode occurring in the monitored activity;

classifying said tachycardia episode as between one of a ventricular tachycardia and a supra-ventricular tachycardia according to a predetermined criteria and a given adjustment of said predetermined criteria;

authorizing delivery of a shock therapy in response to a classified ventricular tachycardia and inhibiting delivery of a shock therapy in response to a classified supra-ventricular tachycardia, and modifying said classifying step, in response to a discriminated atrial fibrillation, by one of adding temporarily at least one criterion and modifying temporarily the adjustment of a predetermined criterion to confirm said discriminated atrial fibrillation as one of genuine and not genuine.

12. The method of claim 11, wherein modifying said discrimination step further comprises providing a supplementary research criterion of at least one of a short RR interval range and a long RR interval range, said one RR interval range being significantly distanced from an RR interval stability zone.

13. The method of claim 12, further comprising defining said RR interval stability zone as having a first limit and a second limit and wherein providing the research criterion further comprises providing a long RR interval range and a short RR interval range respectively separated from the first and second limits by a predetermined interval width on each side of the RR stability zone.

14. The method of claim 11, wherein providing the added criterion further comprises providing a supplementary counting and comparison criterion corresponding to a number of atrial events relative to a number of ventricular events during a given duration.

15. The method of claim 11, wherein providing the modifiable adjustment further comprises providing a majority parameter, evaluating the majority parameter over a number of predetermined cycles, identifying an RR interval and determining the presence of a percentage, greater than or equal to a given threshold, of the identified RR intervals situated outside of a predetermined RR interval stability zone.

16. The method of claim 15, wherein providing the modifiable adjustment further comprises providing a duration parameter of tachycardia persistence.

17. The method of claim 15, wherein providing the modifiable adjustment further comprises providing a width parameter of an RR interval stability zone.

18. The method of claim 11, further comprising restoring the criteria and/or parameters of the classification steps in response to an absence of a classified supra-ventricular tachycardia episode in the monitored activity.

19. The method of claim 11, further comprising determining if one or more criterion are temporarily adjusted and/or the temporarily modified adjustment is in use a determined number of times in the course of a given period, and applying the addition and/or modification in a permanent manner.

20. The method of claim 11 further comprising authorizing an atrial therapy in response to a classified supra-ventricular tachycardia.

* * * * *